United States Patent [19]

Chevigné et al.

[11] Patent Number: 5,246,558

[45] Date of Patent: Sep. 21, 1993

[54] METHOD FOR THE SEPARATION OF GLYCOSYLATED HEMOGLOBIN HB A1C BY AGAROSE GEL ELECTROPHORESIS

[75] Inventors: Roland Chevigné, Wepion; Jacques Janssen, Brussels, both of Belgium

[73] Assignee: Analis S.A., Belgium

[21] Appl. No.: 821,429

[22] Filed: Jan. 15, 1992

[30] Foreign Application Priority Data

Jan. 15, 1991 [BE] Belgium ............................ 09100027

[51] Int. Cl.$^5$ .................. G01N 27/26; G01N 27/447; B01D 57/02
[52] U.S. Cl. ............................... 204/182.8; 204/299 R
[58] Field of Search .............. 204/299 R, 182.8, 182.9

[56] References Cited

U.S. PATENT DOCUMENTS

| | | | |
|---|---|---|---|
| 4,222,836 | 9/1960 | Kerr et al. ........................ | 204/182.8 |
| 4,351,711 | 9/1982 | Ambler ............................ | 204/183.3 |
| 4,578,218 | 3/1986 | Saundry et al. .................... | 530/383 |
| 4,990,597 | 2/1991 | Löbermann .................... | 530/415 K |

FOREIGN PATENT DOCUMENTS 225867 6/1987 European Pat. Off. .
3504385 8/1985 Fed. Rep. of Germany .

OTHER PUBLICATIONS

Kaplan, et al., *Clinical Chemistry, Theory, Analysis and Correlation,* The C. V. Mosby Company, pp. 152-155, 1984.

*Primary Examiner*—John Niebling
*Assistant Examiner*—John S. Starsiak, Jr.
*Attorney, Agent, or Firm*—Knobbe, Martens, Olson & Bear

[57] ABSTRACT

According to the invention, an agarose gel containing chondroitin sulfate is used as a support medium for electrophoresis for separating glycosylated hemoglobin Hb A1c from the other types of hemoglobins.

A densitometric analysis of the gel after electrophoresis enables the percentage of each type of hemoglobin contained in the sample to be quantified.

15 Claims, No Drawings

METHOD FOR THE SEPARATION OF GLYCOSYLATED HEMOGLOBIN HB A1C BY AGAROSE GEL ELECTROPHORESIS

SUBJECT OF THE INVENTION

The present invention relates to an electophoretic method carried out on agarose gel, enabling hemoglobin glycosylated with glucose Hb Alc, present in a blood sample, to be separated not only from unglycosylated hemoglobins but also from the other types of glycosylated hemoglobins, such as Hb Ala and Hb Alb, for example, fetal hemoglobin and, where appropriate, abnormal hemoglobins.

After separation by the method of the invention, a conventional densitometric analysis enables the percentage of each type of hemoglobin present in the sample to be quantified.

TECHNOLOGICAL BACKGROUND

Monitoring of the course of diabetes in a patient may be accomplished by checking the glucose level in the blood. However, changes in this level are known to be especially rapid. Glucose assays can give only sporadic information about the patient's blood sugar level, and hence do not reflect the changes in the latter in the weeks preceding the analysis.

Quantitative determination of glycosylated hemoglobin Hb Al is known, moreover, to reflect a patient's average blood glucose concentration over a period of two months preceding the taking of a blood sample.

For this reason, assays of glycosylated (also termed glycated) hemoglobin are frequently used in medical analysis laboratories.

Hemoglobin consists of four peptide chains with a heme group. The main hemoglobin of normal adult subjects is hemoglobin A, consisting of two $\alpha$ chains and two $\beta$ chains.

Hemoglobin Alc is formed by nonenzymatic glycosylation of the $\beta$ chains of hemoglobin A by the binding of glucose to the free $NH_2$ ends of the N-terminal valines of each $\beta$ chain.

Biochemical analysis shows that this Hb Alc fraction contains one mole of glucose per mole of hemoglobin.

The total glycosylated hemoglobin Al also comprises the fractions Ala, Alb, Ald and Ale. The first contains glucose 6-phosphate instead of unphosphorylated glucose; at the present time, little is yet known about the other three, but there does not appear to be any correlation between these fractions and the blood sugar balance.

SUMMARY OF THE PRIOR ART

Various methods are used for separating the glycosylated hemoglobins.

Several chromatographic methods give a satisfactory result from the standpoint of the result obtained, but are generally slow and expensive.

It is, for example, known to perform affinity chromatography using the property of glycosylated hemoglobin of binding to m-aminophenylboric acid bound to an agarose gel, eluting by means of two suitable buffers.

Chromatography on weakly acid cation exchange resin permits the separation of different hemoglobin fractions on elution by means of buffers of different ionic strength and pH. Such techniques are, for example, described in U.S. Pat. Nos. 4,389,491 and U.S. Pat. No. 4,407,961. These chromatographic techniques are sensitive to temperature variations, and the analyses are often marred by errors with samples containing fetal hemoglobin (HbF) or abnormal hemoglobins (HbS, HbC).

High performance liquid chromatography (HPLC) yields good results, and there are expensive automated analyzers which permit analyses on a mass production basis.

Among electrophoretic techniques, it is known to separate the different components of hemoglobin electrically according to their isoelectric points on a polyacrylamide gel in a pH gradient (separation by isoelectric focusing); this technique enables abnormal hemoglobins to be detected, but HbF interferes with Hb Alc, which migrates to the same point; in addition, a densitometric assay is difficult to apply to this technique. It should be noted that Hb Alc/HbF interference causes problems, in particular, for the monitoring of diabetes in pregnant women.

U.S. Pat. No. 4,222,836 mentions a technique for separation of glycosylated hemoglobins on agar gel containing a citrate buffer. This permits the separation, on the one hand of unglycosylated hemoglobin Ao, and on the other hand of the collective glycosylated hemoglobins Hb Ala, b and c which all migrate to the same point. This technique necessitates strict control of the sulfate content of the agar used.

Similar results obtained by electrophoresis on agar gel are mentioned in the following papers: Menard L et al., Quantitative determination of glycosylated hemoglobin Al by agar gel electrophoresis, in Clin. Chem. 26, 1075 (1979), and Aleyassine H et al., Agar gel electrophoretic determination of glycosylated hemoglobin: effect of variant hemoglobins, hyperlipidemia and temperature, in Clin. Chem. 27/3, 472–475 (1981).

U.S. Pat. No. 4,351,711 (J. Ambler) describes a method of electrophoresis which enables glycosylated hemoglobin to be separated from the other hemoglobin fractions. According to this document, dextran sulfate is included in a blood sample or in the electrophoresis buffer. The support used can be a conventional agar gel or a cellulose acetate gel.

The limitations of this method are stressed by the author of the paper himself (J. Ambler) in "Measurement of Glycosylated Hemoglobin on Cellulose Acetate Membranes by mobile Affinity Electrophoresis" Clin. Chem. 1983, 29, 340-343: namely, the interference of fetal hemoglobin (HbF), the lack of separation of Hb Ala and Hb Alb, the need to stain the gel and hence the impossibility of working on whole blood. It is necessary to used washed hemolysates of red cells, which involves further steps and a vast amount of manpower.

The paper by Aleyassine H., Determination of glycosylated hemoglobin by affinity electrophoresis on agarose gel, in Clinica Chemica Acta, 142, 123-130, (1984), describes an analogous technique which likewise enables a separation of the collective glycosylated hemoglobins from the unglycosylated hemoglobins to be obtained. According to the process described, dextran sulfate is added to an agarose gel. After electrophoresis, the fetal hemoglobin migrates to the same point as the glycosylated hemoglobin, thereby creating interference. Hb Ala and Hb Alb are not separated.

In addition, the author points out in this paper that the results obtained are greatly dependent on the source of dextran sulfate used. The Applicant was, moreover, able to establish that it was possible for different batches of the same grade of dextran sulfate from the same supplier to fail to give results, thereby making it difficult to make use of this technique.

There is hence, at the present time, as far as the Applicant is aware, no electrophoretic method enabling a good separation of glycosylated hemoglobin Hb Alc from unglycosylated hemoglobins and from the other types of glycosylated hemoglobins to be obtained, while not displaying interference with abnormal hemoglobins such as fetal hemoglobin HbF and while enabling the constituents to be assayed by densitometry after the electrophoretic separation.

OBJECTIVES OF THE INVENTION

The objective of the invention is to provide an electrophoretic method enabling such results to be obtained, while being cheap, practical and easy to use.

A further objective of the invention is to provide such a method which also enables different abnormal hemoglobins to be identified.

Another objective of the invention is to provide kits comprising an agarose gel enabling the electrophoretic method of the invention to be performed.

CHARACTERISTIC FEATURES OF THE INVENTION

The subjects of the invention are a method for the preparation of agarose gel in which a sulfated polysaccharide, especially chondroitin sulfate, is added, and the agarose gels capable of being obtained by this method.

The chondroitin sulfate may be chosen from the group comprising chondroitin sulfate A, chondroitin sulfate B, chondroitin sulfate C and a mixture of two or more of these compounds.

The chondroitin sulfate used may be extracted from various animal species: several types are commercially available, it being possible for these to be obtained, for example, from porcine rib or skin, bovine trachea or cornea or shark or whale cartilage.

Tests of electrophoresis with gels containing these different types of chondroitin sulfate, employed alone or mixed, gave good results independently of their origin and their molecular weight. Observation of the gels enabled an identification of glycosylated hemoglobin Hb Alc to be obtained.

The chondroitin sulfate may be contained in an equilibration buffer, advantageously at a concentration of 0.1 to 3% in said buffer, and preferably at a concentration of 0.5 to 1% in said buffer. The pH of the latter is generally between 5 and 6, and preferably between 5.2 and 5.8.

The buffer can contain an acid chosen from maleic, phthalic, 2,3-pyridinedicarboxylic, succinic, dibromosuccinic, mucic, diglycolic, malic and adipic acids, and a base chosen from the following: Tris, NaOH, KOH, DL-methylglucamine, imidazole and piperazine.

It is self-evident that other acceptable acids and bases may be used.

Preferably, the chondroitin sulfate is added to the agarose before solidification of the gel. The gel can also be subjected to equilibration in equilibration buffer containing chondroitin sulfate.

It is hence possible to use in this manner a gel free from chondroitin sulfate, such as, for example, a Beckman paragon® SPE gel, for the identification of glycosylated hemoglobin Hb Alc, without departing from the scope of the invention. The equilibration usually lasts for 30 minutes.

Another subject of the invention is a kit for the electrophoresis of hemoglobin, comprising an agarose gel obtained according to the method of the invention, where appropriate an equilibration buffer containing chondroitin sulfate, and an electrophoresis buffer. Preferably, the electrophoresis buffer is identical to the equilibration buffer (but does not contain, where this is relevant, chondroitin sulfate).

The invention is illustrated by the examples of electrophoretic gels described below (Examples 1 to 7) and by an example of an embodiment (Example 8).

EXAMPLES 1 TO 7 (PREPARATION)

Standard solutions of agarose are prepared in the following manner: 10 g of agarose are poured into 830 ml of distilled water with vigorous stirring. The mixture is heated gradually to 95° C. and then cooled to around 55° C. With stirring, 170 ml of a concentrated solution containing one or more acids or substances behaving as acids, one or more bases, and, where appropriate, a preservative such as sodium azide, for example, are added.

Chondroitin sulfate, as well as known adjuvants enabling the desired gel features (texture, water retention) to be obtained, are added to these standard solutions. After homogenization, the agarose gels (200 to 250 gels measuring 10×7.5 cm) are cast on an appropriate support.

| Ex. | Acid | Base | Azide | Other constituent(s) | Chondroitin sulfate |
|---|---|---|---|---|---|
| 1. | Maleic 8.2 g | TRIS 11.9 g | 0.59 g | — | 7.84 g |
| 2. | Malic 9.2 g | TRIS 14.5 g | 1 g | — | 6.51 g |
| 3. | Maleic 8.7 g | TRIS 11.8 g | 0.21 g | Potassium hydrogen phthalate 1.3 g | 10 g |
| 4. | Phthalic 8.02 g | TRIS 10.8 g | 1 g | MOPSO 10.1 g | 10 g |
| 5. | 2,3-Pyridinedicarboxylic 8 g | TRIS 10.9 g | 1 g | MES 5.04 g | 8.61 g |
| 6. | Maleic 10 g | Imidazole 5.2 g | 0.4 g | NaSCN 2 g | 5.3 g |
| 7. | Maleic 5.47 g | TRIS 7.79 g | — | Potassium hydrogen phthalate 0.82 g NaSCN 1.5 g | 6.47 g |

EXAMPLE 8 (EMBODIMENT)

A gel obtained according to one of the preparations described in Examples 1, 2 and 3 is placed on the bench and blotted to remove the excess buffer. Hemolysates of whole blood or of red cells are applied according to a method which is standard in electrophoresis. The gel is then subjected to an electrophoresis of 50 V for 20 to 40 minutes or 100 V for 10 to 20 minutes, preferably using in the electrophoresis buffer the acids and bases employed for preparation of the standard solution of agarose for manufacture of the gel. After electrophoresis, the gel is rinsed with distilled water and the gel support wiped thoroughly, a densitometric reading is then carried out at 415 nm, enabling the presence of abnormal hemoglobins to be detected and the percentage of glycosylated hemoglobin Hb Alc relative to one or more of the hemoglobins present in the sample to be calculated.

Alternatively, the gel may be dried, and then read by densitometry when dry. A variant can consist in staining the gel so as to enable it to be read with a low-sensitivity densitometer, or to enable it to be filed. This staining may be obtained using a protein-staining reagent (taking it into account that proteins other than hemoglobin may react) or a hemoglobin-specific stain including techniques employing antigen-antibody properties.

Experimental results have shown, in particular, that it is possible, using the gels according to the invention, to demonstrate without possible confusion well-defined bands corresponding to the following hemoglobins: Hb Ao, methemoglobin, Hb A1c, HbF, Hb A1b and Hb A1a.

Although the above examples illustrate advantageous embodiments of the invention, they do not limit the scope of the latter.

In the case where a gel for electrophoresis not containing chondroitin sulfate is at the user's disposal, for example a Beckman paragon® SPE gel, it will not represent a departure from the scope of the invention if such a gel is left to equilibrate, for example for 30 minutes, in an equilibration buffer containing acids and bases as mentioned in the above examples and chondroitin sulfate. Although the method takes longer, the results obtained are altogether similar. Neither will the addition of chondrotin sulfate to an agarose gel containing another sulfated polysaccharide represent a departure from the scope of the invention.

We claim:

1. A method for separating glycosylated hemoglobin Hb A1c from other hemoglobin proteins present in a sample of whole blood or a sample of red blood cells, comprising:
   forming an agarose gel containing a chondroitin sulfate;
   placing said gel in an electrophoresis buffer, said electrophoresis buffer being a pH-balanced solution suitable for electrophoresis of said samples in said agarose gel;
   loading said samples into said gel; and
   subjecting said gel to electrophoresis.

2. A method for separating glycosylated hemoglobin Hb A1c from other hemoglobin proteins present in a sample of whole blood or a sample of red blood cells, comprising:
   forming an agarose gel;
   placing said gel into an equilibrating buffer solution, said equilibrating buffer solution being a pH-balanced solution containing chondroitin sulfate;
   removing said gel from said equilibrating buffer solution and placing it in an electrophoresis buffer, said electrophoresis buffer being a pH-balanced solution suitable for electrophoresis of said samples in said agarose gel;
   loading said samples onto said gel; and
   subjecting said gel to electrophoresis.

3. An agarose gel electrophoresis system for separating species of hemoglobin, comprising:
   an agarose gel which contains a sulfated polysaccharide;
   an equilibration buffer, said equilibrating buffer solution being a pH-balanced solution containing chondroitin sulfate; and
   an electrophoresis buffer, said electrophoresis buffer being a pH-balanced solution suitable for electrophoresis of samples containing said species of hemoglobin in said agarose gel.

4. In an agarose gel electrophoresis system comprising an agarose gel and an electrophoresis buffer in which electrophoresis of a sample loaded on said gel is performed, said electrophoresis buffer being a pH-balanced solution suitable for electrophoresis of samples containing whole blood or red blood cells in said agarose gel, the improvement comprising a chondroitin sulfate in the gel.

5. The electrophoresis system of claim 4, additionally comprising an equilibration buffer, said equilibration buffer being a pH-balanced solution containing a chondroitin sulfate, wherein the chondroitin sulfate is in the gel as a result of equilibration of said gel in said equilibration buffer.

6. The agarose gel electrophoresis system of claim 5, wherein the chondroitin sulfate is present in the electrophoresis buffer at a concentration of 0.1 to 3% in said buffer.

7. The agarose gel electrophoresis system of claim 6, wherein the chondroitin sulfate is present in the buffer at a concentration of 0.5 to 1% in said buffer.

8. The agarose gel electrophoresis system of claim 5, wherein the pH of said equilibration buffer solution is between 5 and 6.

9. The agarose gel electrophoresis system of claim 8, wherein the pH of said equilibration buffer solution is between 5.2 and 5.8.

10. The agarose gel electrophoresis system of claim 5, wherein the equilibration buffer solution contains an acid selected from the group consisting of maleic, phthalic, 2,3-pyridinedicarboxylic, succinic, dibromosuccinic, mucic, diglycolic, malic and adipic acids.

11. The agarose gel electrophoresis system of claim 5, wherein the equilibration buffer solution comprises a base selected from the group consisting of tris(hydroxymethyl)-aminomethane, NAOH, KOH, DL-methylglucamine, imidazole and piperazine.

12. The agarose gel electrophoresis system of claim 4, wherein the chondroitin sulfate is selected from the group consisting of chondroitin sulfate A, chondroitin sulfate B, chondroitin sulfate C, and a mixture of any two or more of the foregoing compounds.

13. The agarose gel electrophoresis system of claim 4, wherein the chondroitin sulfate is added to the agarose solution before it solidifies.

14. A method for the preparation of an agarose gel, comprising:
   making a buffered solution containing sufficient agarose to form a gel;
   adding a sulfated polysaccharide;
   forming a gel therefrom;
   making an equilibration buffer solution, said equilibration buffer solution being a pH-balanced solution containing chondroitin sulfate, wherein said equilibration buffer solution contains an acid selected from the group consisting of maleic, phthallic, 2,3-pyridinedicarboxylic, succinic, dibromosuccinic, mucic, diglycolic, malic, and adipic acids; and
   placing said gel in said equilibration buffer solution.

15. A method for the preparation of an agarose gel, comprising:
   making a buffered solution containing sufficient agarose to form a gel;
   adding a sulfated polysaccharide;

forming a gel therefrom;
making an equilibration buffer solution, said equilibration buffer solution being a pH-balanced solution containing chondroitin sulfate, wherein said equilibration buffer solution comprises a base selected from the group consisting of tris(hydroxymethyl)-aminomethane, NaOH, KOH, DL-methylglucamine, imidazole, and piperazine; and placing said gel in said equilibration buffer solution.

* * * * *